US012142353B2

(12) United States Patent
VanderMolen et al.

(10) Patent No.: US 12,142,353 B2
(45) Date of Patent: Nov. 12, 2024

(54) METHODS AND SYSTEMS FOR PROVIDING IMPROVED MECHANISM FOR UPDATING HEALTHCARE INFORMATION SYSTEMS

(71) Applicant: ViZIENT SUPPLY, LLC, Irving, TX (US)

(72) Inventors: Timothy A. VanderMolen, Lewisville, TX (US); Melanie Polston, Dallas, TX (US)

(73) Assignee: VIZIENT SUPPLY, LLC, Irving, TX (US)

( * ) Notice: Subject to any disclaimer, the term of this patent is extended or adjusted under 35 U.S.C. 154(b) by 429 days.

(21) Appl. No.: 16/985,609

(22) Filed: Aug. 5, 2020

(65) Prior Publication Data

US 2020/0372984 A1    Nov. 26, 2020

Related U.S. Application Data

(63) Continuation of application No. 14/747,389, filed on Jun. 23, 2015, now abandoned.

(51) Int. Cl.
G16H 10/60           (2018.01)
(52) U.S. Cl.
CPC .................. G16H 10/60 (2018.01)
(58) Field of Classification Search
CPC ..................................................... G16H 10/60
See application file for complete search history.

(56) References Cited

U.S. PATENT DOCUMENTS

| | | |
|---|---|---|
| 5,224,034 A | 6/1993 | Katz et al. |
| 5,621,201 A | 4/1997 | Langhans et al. |
| 5,970,475 A | 10/1999 | Barnes et al. |
| 6,032,131 A | 2/2000 | Vogel |
| 6,081,786 A | 6/2000 | Barry et al. |
| 6,092,050 A | 7/2000 | Lungren et al. |
| 6,604,089 B1 | 8/2003 | Van Horn et al. |

(Continued)

OTHER PUBLICATIONS

Office Action for U.S. Appl. No. 13/765,507; dated Jun. 20, 2014.
(Continued)

*Primary Examiner* — Robert A Sorey
*Assistant Examiner* — Kristine K Rapillo
(74) *Attorney, Agent, or Firm* — Greenberg Traurig LLP

(57) ABSTRACT

Methods, systems, and apparatuses for providing improved management of hospital information systems are provided. An example of a method for providing improved management of a hospital information system includes providing an interface for electronic entry of a set of request parameters, the request parameters comprising at least one product identifier for a product to be purchased by a healthcare organization and at least one change to a healthcare information system related to the at least one product, receiving the set of electronic request parameters, generating, via the request management circuitry, an action plan defining at least one action for implementation of the at least one change to the healthcare information system, monitoring, via the request management circuitry, for completion of the at least one action, and in response to detection of completion of the at least one action, implementing the at least one change to the healthcare information system.

7 Claims, 13 Drawing Sheets

(56) References Cited

U.S. PATENT DOCUMENTS

| | | |
|---|---|---|
| 6,697,799 B1 | 2/2004 | Neal |
| 7,043,492 B1 | 5/2006 | Neal |
| 7,146,331 B1 | 12/2006 | Young |
| 7,272,575 B2 | 9/2007 | Vega |
| 7,401,035 B1 | 7/2008 | Young |
| 7,475,034 B2 | 1/2009 | Cayne et al. |
| 7,542,958 B1 | 6/2009 | Warren |
| 7,637,426 B1 | 12/2009 | Green |
| 7,711,749 B2 | 5/2010 | Brodie |
| 7,870,012 B2 | 1/2011 | Katz et al. |
| 7,899,701 B1 | 3/2011 | Odom |
| 7,966,235 B1 | 6/2011 | Capelli et al. |
| 8,195,527 B2 * | 6/2012 | Chowdhary .......... G06Q 10/06 705/26.7 |
| 8,417,715 B1 | 4/2013 | Bruckhaus |
| 8,620,773 B1 | 12/2013 | O'Neil |
| 8,626,692 B2 | 1/2014 | Bauer |
| 8,868,471 B1 | 10/2014 | Hullender |
| 2001/0047299 A1 | 11/2001 | Brewer et al. |
| 2002/0010686 A1 | 1/2002 | Whitesage |
| 2002/0026429 A1 | 2/2002 | Lostis et al. |
| 2002/0069079 A1 | 6/2002 | Vega |
| 2002/0077867 A1 | 6/2002 | Gittins |
| 2002/0133444 A1 | 9/2002 | Sankaran et al. |
| 2002/0174000 A1 | 11/2002 | Katz et al. |
| 2003/0033179 A1 | 2/2003 | Katz et al. |
| 2003/0069818 A1 | 4/2003 | Menninger |
| 2003/0069824 A1 | 4/2003 | Menninger |
| 2003/0074263 A1 | 4/2003 | Hoffman et al. |
| 2003/0074279 A1 | 4/2003 | Viswanath et al. |
| 2003/0177070 A1 | 9/2003 | Viswanath et al. |
| 2003/0208392 A1 | 11/2003 | Shekar et al. |
| 2004/0010463 A1 | 1/2004 | Hahn-Carlson et al. |
| 2004/0073457 A1 | 4/2004 | Kalies |
| 2004/0093326 A1 | 5/2004 | Carson |
| 2004/0172393 A1 | 9/2004 | Kazi |
| 2004/0220861 A1 | 11/2004 | Morciniec et al. |
| 2004/0220887 A1 | 11/2004 | Byde et al. |
| 2004/0225486 A1 | 11/2004 | Mullis et al. |
| 2004/0230512 A1 | 11/2004 | Gulati |
| 2005/0049938 A1 | 3/2005 | Venkiteswaran |
| 2005/0144122 A1 | 6/2005 | Creveling |
| 2006/0041496 A1 | 2/2006 | Amin |
| 2006/0047574 A1 | 3/2006 | Sundaram |
| 2006/0085544 A1 | 4/2006 | Chen et al. |
| 2006/0095333 A1 | 5/2006 | Gambhir |
| 2006/0200477 A1 | 9/2006 | Barrenechea |
| 2006/0206352 A1 | 9/2006 | Pulianda |
| 2006/0271405 A1 | 11/2006 | Cipolle et al. |
| 2007/0033098 A1 | 2/2007 | Peters et al. |
| 2007/0067218 A1 | 3/2007 | Bingham |
| 2007/0083650 A1 | 4/2007 | Collomb et al. |
| 2007/0106563 A1 | 5/2007 | Okada et al. |
| 2007/0136126 A1 | 6/2007 | Notani et al. |
| 2007/0156572 A1 | 7/2007 | Lites |
| 2007/0162303 A1 | 7/2007 | Wiley et al. |
| 2007/0208210 A1 | 9/2007 | Gelfand et al. |
| 2007/0240717 A1 | 10/2007 | Kaczka et al. |
| 2007/0250341 A1 | 10/2007 | Howe |
| 2007/0276710 A1 | 11/2007 | Hudgeon et al. |
| 2007/0288344 A1 | 12/2007 | Dalal et al. |
| 2007/0293932 A1 | 12/2007 | Zilla et al. |
| 2008/0010185 A1 | 1/2008 | Kirkpatrick |
| 2008/0077506 A1 | 3/2008 | Rampell et al. |
| 2008/0140492 A1 | 6/2008 | Rousso et al. |
| 2008/0167901 A1 | 7/2008 | Betz |
| 2008/0208616 A1 | 8/2008 | Young |
| 2009/0012854 A1 | 1/2009 | Altice |
| 2009/0055431 A1 | 2/2009 | Brodie |
| 2009/0055887 A1 | 2/2009 | Brodie |
| 2009/0089625 A1 | 4/2009 | Kannappan et al. |
| 2009/0125415 A1 | 5/2009 | Gindlesperger |
| 2009/0144117 A1 | 6/2009 | Cavander et al. |
| 2009/0216748 A1 | 8/2009 | Kravcik |
| 2009/0234710 A1 | 9/2009 | Belgaied Hassine et al. |
| 2009/0265279 A1 | 10/2009 | Mintz et al. |
| 2009/0288163 A1 | 11/2009 | Jacobson et al. |
| 2010/0005346 A1 | 1/2010 | Hamlescher et al. |
| 2010/0023340 A1 | 1/2010 | Chowdhary et al. |
| 2010/0042431 A1 | 2/2010 | O'Connor et al. |
| 2010/0106652 A1 | 4/2010 | Sandholm et al. |
| 2010/0280963 A1 | 11/2010 | Fordyce, III et al. |
| 2010/0305975 A1 | 12/2010 | Daya |
| 2010/0325010 A1 | 12/2010 | Gindlesperger |
| 2010/0332311 A1 | 12/2010 | Jilk |
| 2011/0016407 A1 | 1/2011 | Nelson |
| 2011/0082723 A1 | 4/2011 | Governatori et al. |
| 2011/0131030 A1 | 6/2011 | McCoy et al. |
| 2011/0173093 A1 | 7/2011 | Psota |
| 2011/0246274 A1 | 10/2011 | Mesaros |
| 2012/0016764 A1 | 1/2012 | Ouimet |
| 2012/0029974 A1 | 2/2012 | Councill |
| 2012/0059680 A1 | 3/2012 | Guthrie et al. |
| 2012/0095949 A1 | 4/2012 | Bauer |
| 2012/0143721 A1 | 6/2012 | Hutchinson et al. |
| 2012/0203650 A1 | 8/2012 | Burlin |
| 2012/0203708 A1 | 8/2012 | Psota et al. |
| 2012/0203785 A1 | 8/2012 | Awada |
| 2013/0110606 A1 | 5/2013 | Seyhan et al. |
| 2013/0203025 A1 | 8/2013 | Cantrell et al. |
| 2013/0204670 A1 | 8/2013 | Chodavarapu et al. |
| 2013/0246118 A1 | 9/2013 | Dyess |
| 2013/0246127 A1 | 9/2013 | Denton |
| 2013/0246217 A1 * | 9/2013 | Denton .............. G06Q 30/0623 705/26.7 |
| 2013/0246221 A1 | 9/2013 | Denton |
| 2013/0246237 A1 | 9/2013 | Dyess |
| 2013/0249176 A1 | 9/2013 | Chang |
| 2014/0088981 A1 | 3/2014 | Momita |
| 2014/0143276 A1 | 5/2014 | Rogers et al. |
| 2014/0187213 A1 | 7/2014 | Shuster et al. |
| 2014/0188541 A1 | 7/2014 | Goldsmith et al. |
| 2014/0222444 A1 | 8/2014 | Cerello et al. |
| 2014/0266041 A1 | 9/2014 | Ghosh et al. |
| 2014/0316940 A1 | 10/2014 | Kirchenbauer |
| 2015/0019361 A1 | 1/2015 | Denton |
| 2015/0180759 A1 | 6/2015 | Fallon |
| 2015/0193709 A1 | 7/2015 | Badu |
| 2015/0301698 A1 | 10/2015 | Roques |
| 2016/0080422 A1 | 3/2016 | Belgodere et al. |
| 2016/0255466 A1 | 9/2016 | Shuster et al. |
| 2016/0379158 A1 | 12/2016 | VanderMolen |
| 2018/0144428 A1 | 5/2018 | Dyess |

OTHER PUBLICATIONS

Office Action for U.S. Appl. No. 13/7655,271; dated Nov. 18, 2014.
Office Action for U.S. Appl. No. 13/765,507; dated Jan. 30, 2015.
Office Action for U.S. Appl. No. 13/765,479; dated Feb. 11, 2015.
Office Action for U.S. Appl. No. 13/765,443; dated Mar. 2, 2015.
Office Action for U.S. Appl. No. 13/765,271; dated Apr. 24, 2015.
Office Action for U.S. Appl. No. 13/765,271; dated Aug. 25, 2015.
Office Action for U.S. Appl. No. 13/765,507; dated Oct. 9, 2015.
Office Action for U.S. Appl. No. 13/765,479; dated Oct. 7, 2015.
Office Action for U.S. Appl. No. 13/835,878; dated Oct. 5, 2015.
Office Action for U.S. Appl. No. 13/765,271; dated Feb. 22, 2016.
Office Action for U.S. Appl. No. 13/835,878; dated Jun. 3, 2016.
Office Action for U.S. Appl. No. 13/765,479; dated Jun. 23, 2016.
Office Action for U.S. Appl. No. 13/765,507; dated Aug. 25, 2016.
Office Action for U.S. Appl. No. 13/765,271; dated Sep. 15, 2016.
Nevada Ex Rel. Steinke v. Merck Co. 432 F. Supp.2d. 1082 (D. Nev. 2006), May 31, 2006.
Notice of Related Applications for filed for U.S. Appl. No. 14/747,389; Jun. 4, 2019; 2 pages; US.

* cited by examiner

METHODS AND SYSTEMS FOR PROVIDING IMPROVED MECHANISM FOR UPDATING HEALTHCARE INFORMATION SYSTEMS

CROSS REFERENCE

This application is a continuation of U.S. patent application Ser. No. 14/747,389, filed Jun. 23, 2015, the entire contents of which are incorporated by reference herein.

TECHNOLOGICAL FIELD

Example embodiments of the present invention relate generally to healthcare information systems and, more particularly, to methods, systems, and apparatuses for providing improved mechanisms for updating healthcare information systems such as electronic item masters and charge masters.

BACKGROUND

The applicant has discovered problems with current methods, systems, and apparatuses for managing electronic healthcare information systems. Through applied effort, ingenuity, and innovation, Applicant has solved many of these identified problems by developing a solution that is embodied by the present invention, which is described in detail below.

BRIEF SUMMARY

Accordingly, a method, apparatus, and computer program are provided to manage healthcare information systems. Example embodiments may include methods, systems, apparatuses, and the like that provide a management interface that allows for adding, deleting, and updating items in a healthcare information system. Embodiments may provide an analysis system that is capable of receiving change requests, generating an action plan comprising configuration changes to electronic systems operable to implement the change request, and monitoring electronic communications to measure the impact and compliance with change request.

Embodiments include a method for implementing changes to electronic healthcare information systems using a healthcare information analysis system. The method includes providing an interface for electronic entry of a set of request parameters, the request parameters comprising at least one product identifier for a product to be purchased by a healthcare organization and at least one change to a healthcare information system related to the at least one product, receiving, via request management circuitry of the healthcare information analysis system, the set of electronic request parameters, generating, via the request management circuitry, an action plan defining at least one action for implementation of the at least one change to the healthcare information system, monitoring, via the request management circuitry, for completion of the at least one action, and, in response to detection of completion of the at least one action, implementing, via healthcare information system interface circuitry of the healthcare information analysis system, the at least one change to the healthcare information system.

The method may also include monitoring, via transactional management circuitry, one or more transactions performed between the healthcare information system and a procurement information system, wherein the one or more transactions include a purchase of the at least one product. The method may also include calculating a financial impact as a result of the at least one change and the one or more transactions, and providing an interface displaying the financial impact. The method may include receiving product information related to the at least one product from a procurement information system separate from the healthcare information analysis system and the healthcare information system, wherein the action plan is generated based at least in part using the product information. The product information may include at least one product cross-reference for the at least one product. The procurement information system may include a product ordering system. The healthcare information system may be at least one of an item master, a charge master, or a formulary.

Embodiments also include an apparatus for implementing changes to electronic healthcare information systems. The apparatus includes request management circuitry and healthcare information system interface circuitry. The request management circuitry is configured to provide an interface for electronic entry of a set of request parameters, the request parameters comprising at least one product identifier for a product to be purchased by a healthcare organization and at least one change to a healthcare information system related to the at least one product, receive the set of electronic request parameters, generate an action plan defining at least one action for implementation of the at least one change to the healthcare information system, monitor for completion of the at least one action, and notify healthcare information system interface circuitry of the completion of the at least one action. The healthcare information system interface circuitry is configured to, in response to detection of completion of the at least one action, implementing, via healthcare information system interface circuitry of the healthcare information analysis system, the at least one change to the healthcare information system.

The apparatus may include transactional management circuitry configured to monitor one or more transactions performed between the healthcare information system and a procurement information system, the one or more transactions comprising a purchase of the at least one product. The request management circuitry may be further configured to calculate a financial impact as a result of the at least one change and the one or more transactions, and provide an interface displaying the financial impact. The request management circuitry may be further configured to receive product information related to the at least one product from a procurement information system separate from the healthcare information analysis system and the healthcare information system, wherein the action plan is generated based at least in part using the product information. The product information may include at least one product cross-reference for the at least one product. The procurement information system may include a product ordering system. The healthcare information system may be at least one of an item master, a charge master, or a formulary.

Embodiments also include a non-transitory computer readable storage medium comprising instructions that, when executed by a processor, cause the processor to implement changes to electronic healthcare information systems using a healthcare information analysis system. The instructions cause the processor to provide an interface for electronic entry of a set of request parameters, the request parameters comprising at least one product identifier for a product to be purchased by a healthcare organization and at least one change to a healthcare information system related to the at least one product, receive the set of electronic request parameters, generate an action plan defining at least one action for implementation of the at least one change to the healthcare information system, monitor for completion of the at least one action, and in response to detection of completion of the at least one action, implement the at least one change to the healthcare information system.

The computer readable storage medium may also include instructions that cause the processor to monitor one or more transactions performed between the healthcare information system and a procurement information system, the one or more transactions comprising a purchase of the at least one product. The computer program product may also include instructions that cause the processor to calculate a financial impact as a result of the at least one change and the one or more transactions, and provide an interface displaying the financial impact. The computer readable storage medium may include instructions that cause the processor to receive product information related to the at least one product from a procurement information system separate from the healthcare information analysis system and the healthcare information system, wherein the action plan is generated based at least in part using the product information. The product information may include at least one product cross-reference for the at least one product. The procurement information system may include a product ordering system.

The above summary is provided merely for purposes of summarizing some example embodiments to provide a basic understanding of some aspects of the invention. Accordingly, it will be appreciated that the above-described embodiments are merely examples and should not be construed to narrow the scope or spirit of the invention in any way. It will be appreciated that the scope of the invention encompasses many potential embodiments in addition to those here summarized, some of which will be further described below.

BRIEF DESCRIPTION OF THE DRAWINGS

Figure 1:
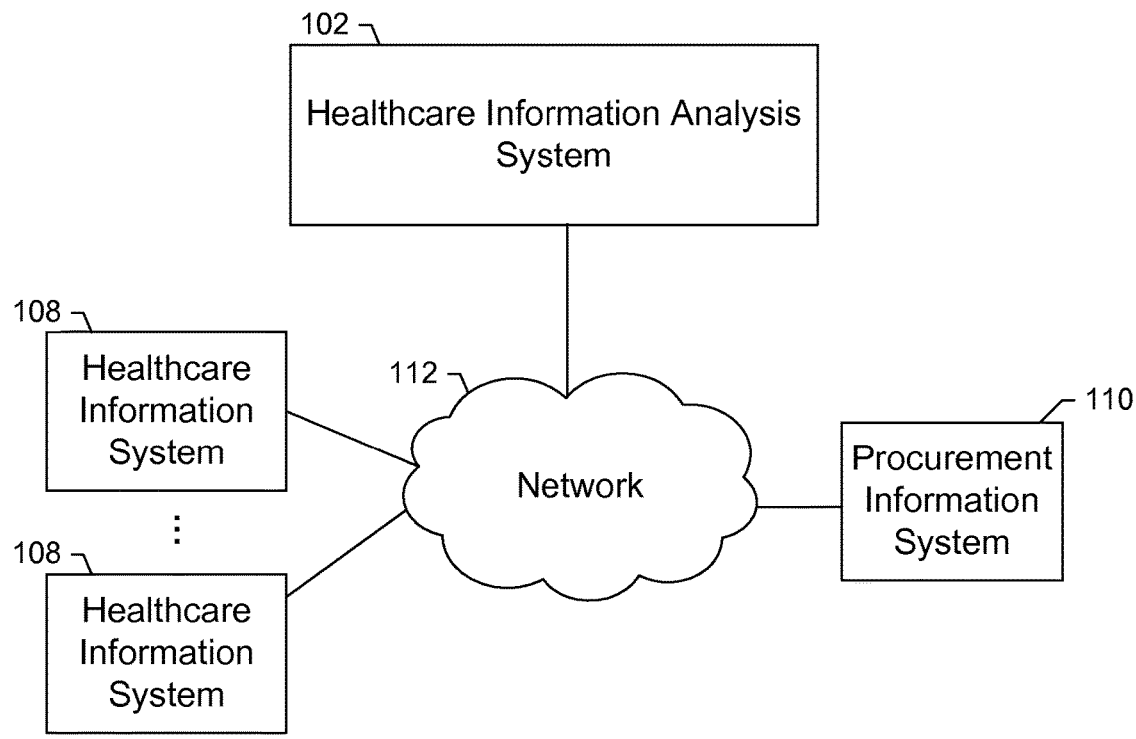
Figure 2:
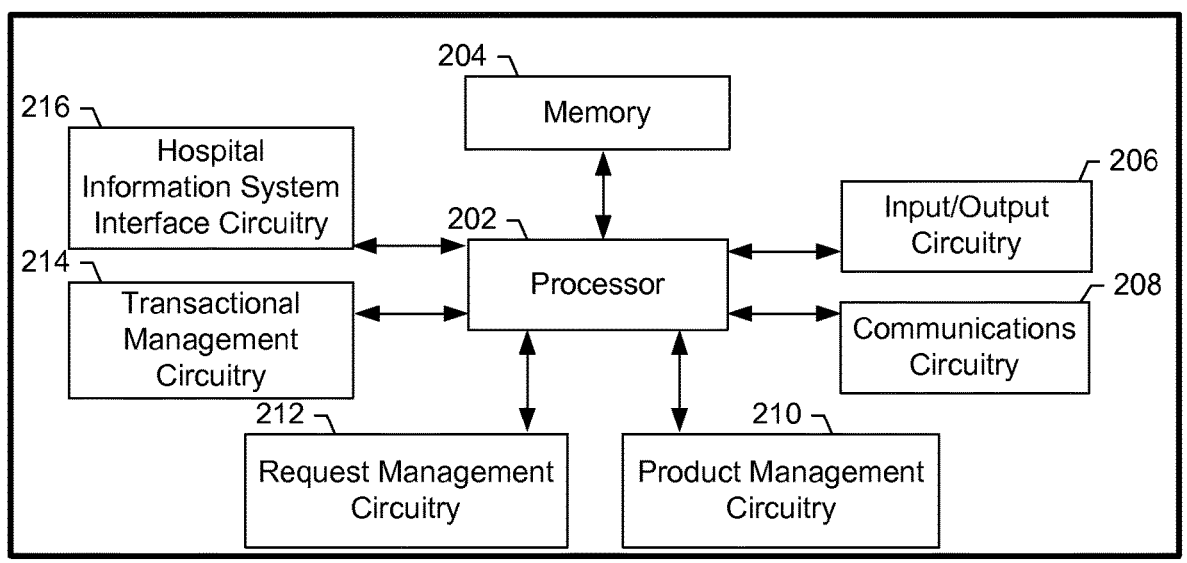
Figure 3:
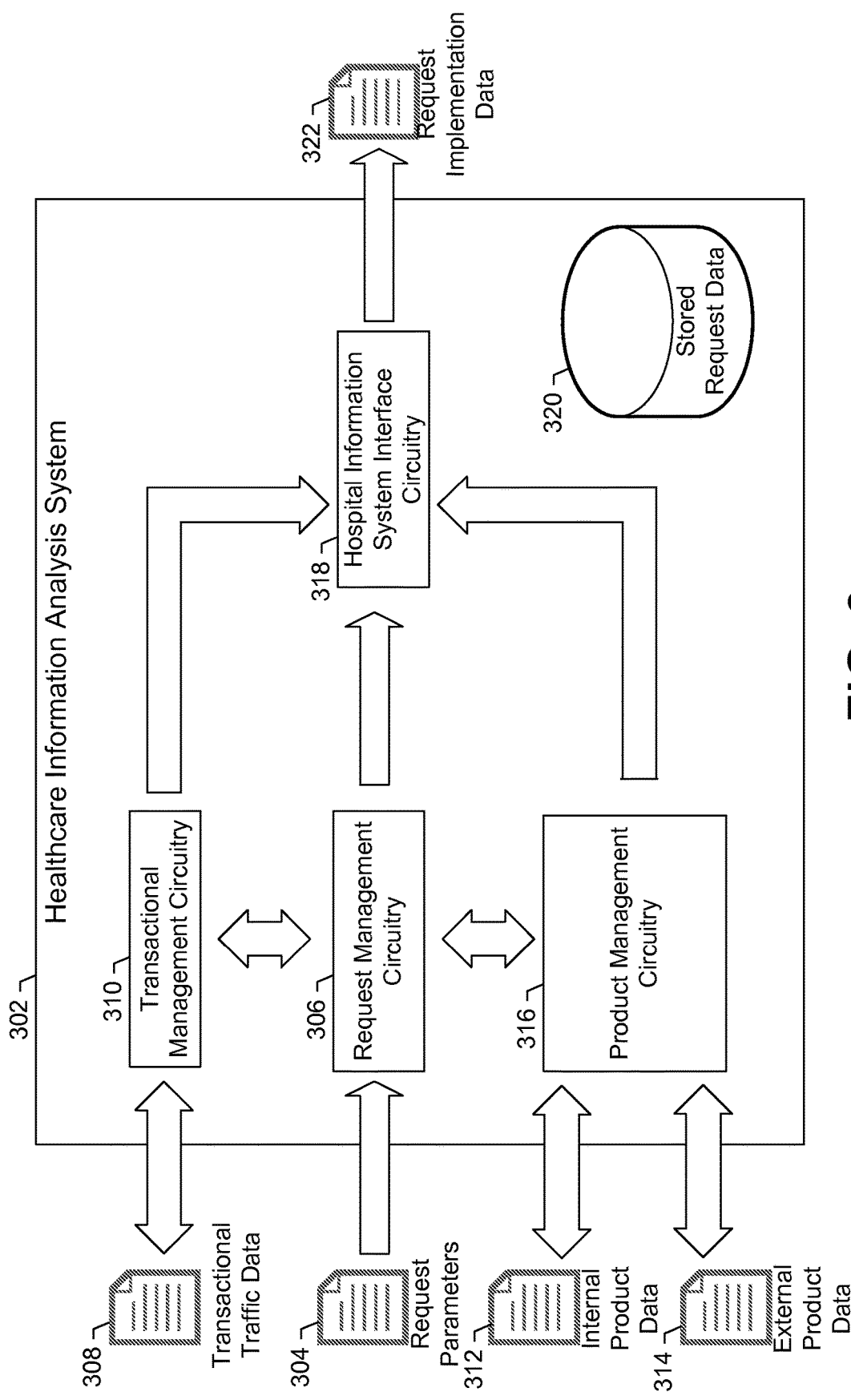
Figure 13:
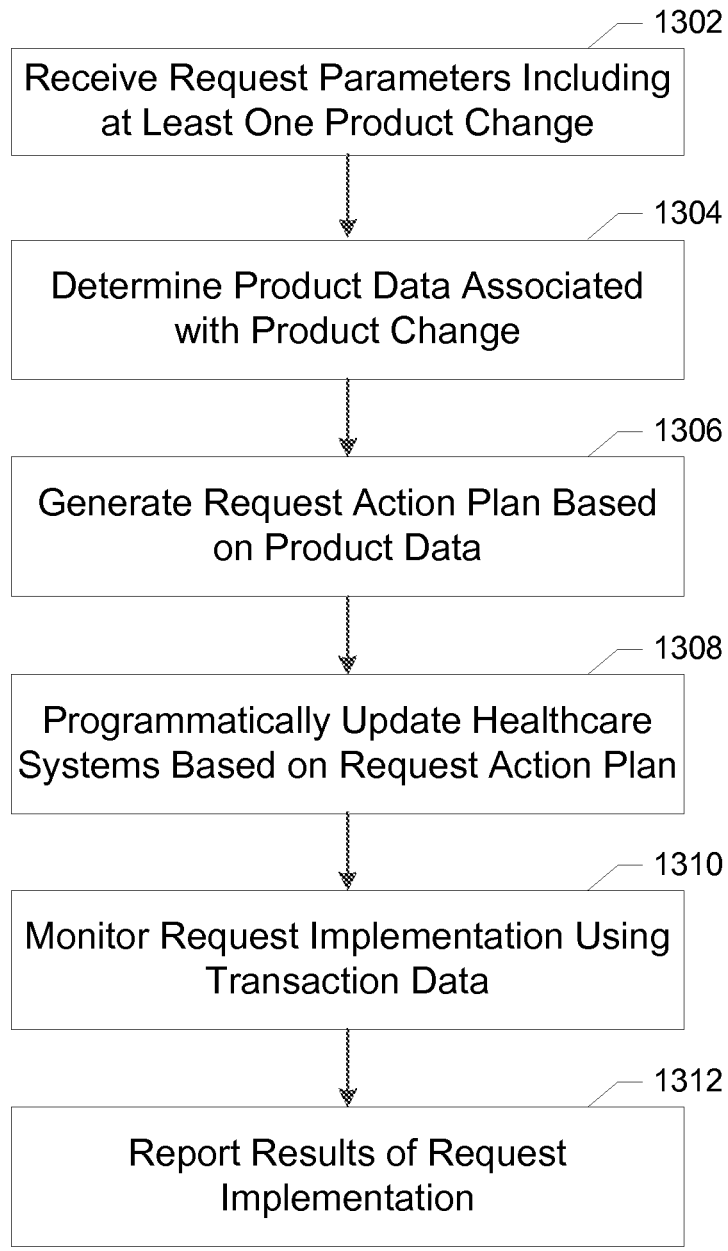
Figure 14:
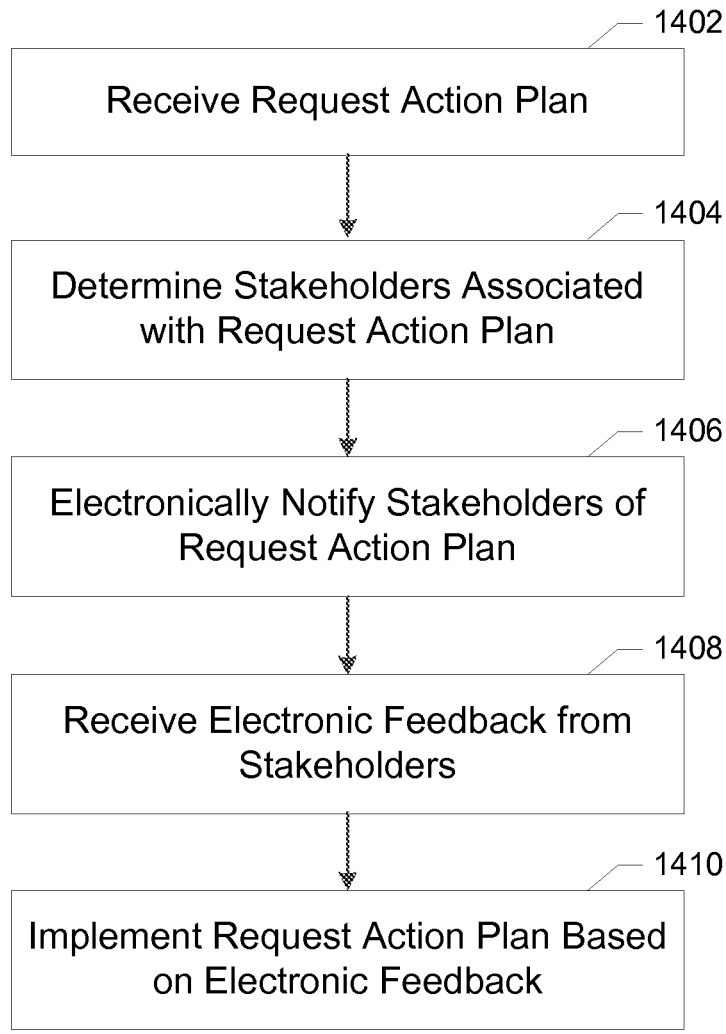

Having thus described certain example embodiments of the present disclosure in general terms, reference will now be made to the accompanying drawings, which are not necessarily drawn to scale, and wherein:

FIG. 1 illustrates an example system within which embodiments of the present invention may operate;

FIG. 2 illustrates a block diagram showing an example device for implementing changes to a healthcare information system using special-purpose circuitry in accordance with some exemplary embodiments of the present invention;

FIG. 3 illustrates an example data flow among components of a healthcare information system in accordance with some exemplary embodiments of the present invention;

FIGS. 4-12 are illustrations of example interfaces for managing a change to a healthcare information system in accordance with some exemplary embodiments of the present invention;

FIG. 13 illustrates a flow diagram depicting an example of a method for managing a change to a hospital information system in accordance with some exemplary embodiments of the present invention; and FIG. 14 illustrates a flow diagram depicting an example of a method for implementing a request action plan in accordance with some exemplary embodiments of the present invention.

DETAILED DESCRIPTION

Overview

Various embodiments of the present invention are directed to improved apparatuses, methods, and computer readable media for managing changes to healthcare information systems. In this regard, embodiments of the present invention provide systems, devices, and frameworks that receive, process, and monitor requested changes to various healthcare information systems such as electronic item masters and charge masters. Embodiments may further interface with remote systems to obtain electronic data about particular products associated with a change request. Embodiments may also monitor electronic data relating to product purchases and other acquisitions to monitor implementation of a proposed change request and to verify compliance with a change request. Embodiments may also provide workflow management tools for managing implementation of a change request and providing feedback to a change request. Some embodiments may provide the ability to interface with remote analysis systems and/or healthcare information systems to "crowd-source" information relating to implementation of the change request.

Definitions

Some embodiments of the present invention will now be described more fully hereinafter with reference to the accompanying drawings, in which some, but not all embodiments of the invention are shown. Indeed, the invention may be embodied in many different forms and should not be construed as limited to the embodiments set forth herein; rather, these embodiments are provided so that this disclosure will satisfy applicable legal requirements. Like numbers refer to like elements throughout.

As used herein, the terms "data," "content," "information," and similar terms may be used interchangeably to refer to data capable of being transmitted, received, and/or stored in accordance with embodiments of the present invention. Thus, use of any such terms should not be taken to limit the spirit and scope of embodiments of the present invention. Further, where a computing device is described herein to receive data from another computing device, it will be appreciated that the data may be received directly from the another computing device or may be received indirectly via one or more intermediary computing devices, such as, for example, one or more servers, relays, routers, network access points, base stations, hosts, and/or the like, sometimes referred to herein as a "network." Similarly, where a computing device is described herein to send data to another computing device, it will be appreciated that the data may be sent directly to the another computing device or may be sent indirectly via one or more intermediary computing devices, such as, for example, one or more servers, relays, routers, network access points, base stations, hosts, and/or the like.

In the context of this application, the term "product" should be understood not only to encompass individual items provided by the supplier, but also sets of items (e.g., several items sold as a group or kit), services (e.g., labor or staffing needs), and various other tangible and intangible goods and services which may be procured according to a supply contract. Examples of these products may include medical supplies and devices, physician preference items, pharmaceuticals, capital, services, and the like.

As used herein, the term "category" should be understood to include particular groupings or organizations of products. Categories may be defined based on the type of product, the intended use of the product, or the like. For example, in the case of medical supplies and devices, products may be identified as belonging to a particular United Nations Standard Products and Services Code (UNSPSC), or a Product Spend Category as provided by Novation Inc. of Irving, Texas. A category may be a pre-defined collection of one or more, and typically a plurality of, UNSPSCs. Categories may be pre-defined for a particular market ecosystem or may be pre-defined by the market. For example, products may be assigned to particular categories by the functionality of the product (e.g., products that protect the user from a particular hazard), by the construction of the product (e.g., products made of latex), by the intended use of the product (e.g., products used by surgeons during a heart surgery), general industrial knowledge, or by any other set of criteria. These categories may be established by an owner or maintainer of the market platform, or in communication with suppliers and/or buyers of the products. Product associations with particular categories may be mutually exclusive, such that any given product may only be associated with a single category.

Embodiments may also leverage knowledge of pre-defined or programmatically defined "cross-references" between products. As used herein, the term "cross-reference" is generally understood to refer to a relationship between products which have the same or similar functional characteristics (e.g., a functional equivalency) such that one product may be used in place of the other in a medical context. A product may be described as a "cross-reference" or a "valid cross-reference" of another product if those products are functionally equivalent to one another. Cross-references between products may occur within sets of products offered by the same manufacturer (e.g., products that only differ in non-functional characteristics, such as color), and cross-references may be provided across manufacturers (e.g., between two manufacturers that both make functionally equivalent latex gloves, those latex gloves would be described as cross-references to one another or having a cross-reference). Embodiments may include mechanisms for identifying cross-references from various sources, including based on previous spending data, based on requests generated by users, based on crowd-sourced data, based on information received from remote healthcare information systems, or the like.

In the context of the present application, the use of the term "healthcare information system" is intended to refer to an electronic, computer-implemented system for managing access to healthcare data. The term "procurement system" is intended to refer to a specialized subset of healthcare information systems related to the procurement of products for use in a healthcare setting. Example procurement systems include electronic, computer-implemented systems for submitting orders, generating invoices, maintaining item masters, maintaining formularies, maintaining product cross-reference lists, providing payment information, and the like.

In the context of the present application, the use of the term "item master" is understood to refer to electronic healthcare information systems that implement listings of products available to order by a healthcare organization. The use of the term "charge master" is understood to refer to electronic healthcare information systems that implement prices for particular products and services offered by a healthcare organization.

Technical Underpinnings and Implementation of Exemplary Embodiments

Healthcare organizations (HCOs) have been dramatically affected by the decreasing cost and increasing processing power of modem computers. The move toward electronic medical records and electronic ordering and processing has dramatically increased the information available to HCOs about their own operations and those of others in the field. Product orders, which previously would have been filled out by hand and mailed or faxed to sellers, may now be completed electronically through e-commerce interfaces, whether over the Internet or through direct interface with seller systems by HCOs. However, although the use of technology has streamlined some aspects of the ordering of products by HCOs, certain mandatory aspects of the HCO ordering system remain as pain points for users.

In particular, the process of reviewing and approving certain products to be used by HCOs requires management of systems known as "item masters" and "charge masters". The "item master" refers to a list of products that are eligible to be used by the HCO. Before a product is added to a HCO item master, the product must go through a review and approval process to ensure it meets the needs of the HCO in terms of functionality, cost, and availability. Such verification is particularly important in the HCO context to ensure that practitioners are provided with appropriate products to perform their jobs while also keeping costs down. For example, careful selection of items to be added to the item master allows HCOs to implement product procurement plans that offer coverage of all possible medical scenarios while taking into account bulk purchasing discounts, limited product storage space, and other costs and benefits related to product procurement. Similarly, charge masters refer to schedules of fees charged to consumers associated with particular products and services offered by the HCO.

In an effort to improve billing and ordering practices for products used by HCOs, many HCOs now utilize electronic item master and charge master systems. In the context of the present application, the functionality offered by embodiments of the present invention is intended to refer and relate to management and interaction with these and other electronic systems, and it should be understood that manual process improvement procedures and changes to written item master systems are not intended to be covered by the scope of the present application.

Furthermore, HCOs may include electronic systems capable of providing electronic formularies that list products which are considered "preferred" products by the HCO. Similarly to adding products to an item master, the addition of particular products to a formulary is often a decision that is subject to review and approval to ensure that products included in the formulary meet certain standards for effectiveness, cost, and the like.

HCOs also are faced with the ability to purchase products from a wide variety of suppliers. Multiple suppliers may provide products that are capable of meeting particular needs of the HCO. However, it may be difficult for the HCO to determine which products from which suppliers are equivalent to meet the needs of the HCO. Accordingly, it may not be readily apparent which products from one supplier may be replaced with products of another supplier. Before replacing a particular product within the item master or adding another product as a valid replacement, HCOs must carefully consider whether the two products are valid cross-references for one another. In some cases, a product may be a valid cross-reference for some uses, but not others.

It should be readily apparent that changes to procurement systems are typically not undertaken lightly, as the use of a new or replacement product may interfere with carefully designed procurement plans. Additionally, HCOs have a strong interest in reviewing and approving products before they are made available for ordering to ensure that the products satisfy the functional and cost needs for the HCO. Embodiments of the present invention address these needs by providing electronic systems that process and analyze electronic data generated by and provided to HCOs for the purpose of managing requests to implement changes to healthcare information systems such as item masters, item formularies, charge masters, and the like.

The inventors have identified these problems and others related to the use of hospital information systems, with particular reference to problems surrounding procurement systems. Furthermore, existing procurement systems lack the ability to access similar electronic data from other HCOs, to communicate with remote procurement information systems, or to provide for electronic management of workflow related to changes to healthcare information systems.

In response to these problems and other problems, the inventors have recognized a need for methods, systems, and apparatuses that provide for electronic management of change requests generated to add, replace, or modify items listed in a HCO item master and other procurement systems. Embodiments leverage access to electronically gathered information to both automate functionality that was previously performed manually and to provide entirely new functionality related to data gathering and evaluation of change requests to procurement systems. Particular embodiments may interface with external systems, such as procurement information systems to access data that was previously not available for consideration in evaluation of change requests. Embodiments may further provide for the ability to manage the entire change request workflow. Embodiments generate and provide access to data related to the change request, the expected impacts of the change request, and feedback from stakeholders. Embodiments further leverage novel analysis techniques for determining the overall value proposition of a given change request utilizing access to data that was previously unavailable to users.

Embodiments further provide technological improvements to existing healthcare information systems by providing novel electronic interfaces and communication techniques between various healthcare information systems, and, in particular, procurement systems, to provide the functionality described herein.

System Architecture

Methods, apparatuses, and computer program products of the present invention may be embodied by any of a variety of devices. For example, the method, apparatus, and computer program product of an example embodiment may be embodied by a networked device, such as a server or other network entity, configured to communicate with one or more devices, such as one or more client devices. Additionally or alternatively, computing devices may include fixed computing devices, such as a personal computer or a computer workstation. Still further, example embodiments may be embodied by any of a variety of mobile terminals, such as a portable digital assistant (PDA), mobile telephone, smartphone, laptop computer, tablet computer, or any combination of the aforementioned devices.

In this regard, FIG. 1 discloses an example computing system within which embodiments of the present invention may operate. Embodiments may include a healthcare information analysis system 102 in communication with one or more healthcare information systems 108 and a procurement information system 110 via a network 112.

The present exemplary embodiment describes a healthcare information analysis system 102 that is separate and distinct from the one or more healthcare information systems 108. The healthcare information analysis system 102 may include a computer or computers as known in the art. For example, the healthcare information analysis system 102 may include one or more servers located at a data center, at a HCO, or the like. Such healthcare information analysis systems 102 may communicate directly or indirectly with such healthcare information systems 108 via a network. For example, an application executing remotely from a healthcare information system or systems may be located at a different data center, such as a data center operated by a third party external to the HCO. For example, the healthcare information analysis system 102 may be an application or applications operated by a procurement service, a supplier, or other party that facilitates the purchasing of products used by HCOs. Such a healthcare information analysis system 102 may provide information and management of change requests via electronic interfaces such as application programming interfaces (APIs) and the like. In some embodiments, the healthcare information analysis system 102 may further provide a web or Internet-based "dashboard" interface allowing users to view the status of change requests via a web browser executing on a client device.

In other embodiments, the healthcare information analysis system 102 may be located onsite to the HCO and operated directly by the HCO. For example, the healthcare information analysis system 102 may be implemented as one or more applications or components executing on the same computing node or nodes as the healthcare information system 108.

Regardless of the location at which the healthcare information analysis system 102 is implemented, the healthcare information analysis system may receive data from the healthcare information systems 108 and the procurement information system 110. Data received from the health information systems 108 may include a variety of electronic data related to management of the healthcare information systems 108 and procurement of products by the HCO. For example, the healthcare information analysis system 102 may monitor or otherwise track electronic data relating to the ordering of products by the HCO. The healthcare information analysis system 102 may identify particular products from orders submitted by the HCOs via the health information systems 108. In some embodiments, orders are sent from the healthcare information systems 108 to the procurement information system 110, and the procurement information system 110 facilitates processing of the order and shipment of the products. In such embodiments, the healthcare information analysis system 102 may receive a duplicate copy of data sent to the procurement information system 110 in this manner, such that the same data is transmitted to the healthcare information analysis system 102 and the procurement information system 110. In other embodiments, the healthcare information system 108 may be provided with product ordering data by the procurement information system 110 without the healthcare information system 108 having to send a separate copy of the data to the healthcare information analysis system 102.

The healthcare information analysis system 102 may also be operable to receive one or more change requests related to one or more of the healthcare information systems 108. Change requests may relate to the addition, deletion, or modification to products offered by one or more components of the health care information systems 108. For example, change requests may relate to the addition of products to a HCO item master or formulary, addition of new cross-references for products ordered by an HCO, requests for evaluation of a financial impact of adding a new product to the healthcare information system (e.g., gathering data related to a particular product or associated cross-reference products without actually adding the product), or the like.

Upon receiving a change request, the healthcare information analysis system 102 may perform processing to implement elements of the change request. For example, the healthcare information analysis system 102 may obtain data related to products indicated in the change request from the procurement information system 110. Depending upon the type of change request, the healthcare information analysis system 102 may generate checklists and/or action plans associated with evaluating and/or implementing the change request. Example interactions for processing a change request are described further below with respect to FIGS. 2-13.

The healthcare information systems 108 may include electronic systems associated with one or more HCOs. It should be appreciated that some HCOs may include multiple separate entities that pool together product purchases. For example, a single HCO entity from a procurement perspective may include multiple hospitals, clinics, or the like. In some embodiments, each of these disparate entities may have a separate healthcare information system 108 that interacts with the healthcare information analysis system 102. The healthcare information analysis system 102 may thus be associated only with an entity or entities related to a particular HCO, such that the particular HCO has its own installation of the healthcare information analysis system 102.

Alternatively, in some embodiments the healthcare information analysis system 102 may be associated with a plurality of separate HCOs that are otherwise unrelated. In such embodiments, the healthcare information analysis system 102 may be implemented by a third party entity (e.g., a procurement provider) for the benefit of the HCOs in making purchases via the third party entity. In yet further embodiments, a third party may implement the healthcare information analysis system 102 and charge for access to the healthcare information system 102, such as by charging a subscription, a one-time fee, or the like.

The healthcare information systems 108 may include a variety of healthcare system components, including but not limited to an item master, a formulary, a charge master, and/or the like. The healthcare information systems 108 may provide the healthcare information analysis system 102 with a mechanism to make changes to the healthcare information systems 108, such as via an API, via direct access to files containing product data, or the like. In some embodiments, data from the healthcare information systems 108 is received as a file or set of files reflecting the contents or some subset of the contents of data stored by the healthcare information systems 108. Embodiments may generate an output file to support modifications to the healthcare information systems 108. For example, embodiments may generate a file in an Electronic Data Interchange (EDI) 832 format. This file may be provided back to the healthcare information systems 108 to propagate any changes to the healthcare information systems 108 as a result of the actions of the healthcare information analysis system 102.

The procurement information system 110 includes data relating to particular products that may be purchased by a HCO. In particular, the procurement information system 110 may include a list of products offered by suppliers that are associated with a procurement system that offers the procurement information system 110. The procurement information system 110 may include or be implemented in conjunction with a system that allows HCOs to purchase products from suppliers via an electronic interface. In some embodiments, the entity operating the procurement information system 110 may also operate the healthcare information analysis system 102.

Product data provided by the procurement information system 110 may include data related to the features, functionality, cross-references, and costs of particular products offered by various suppliers. Product data may also include data relating to product cross-references suggested by a third party entity, product cross-references used by other HCOs, product cross-references suggested by the procurement information system 110, product packaging information, product category information (e.g., which categories a product falls within), spending by other HCOs, responses to questionnaires and assessments related to particular products and product categories, HCO product description (i.e., product descriptors for internal HCO systems such as the healthcare information system 108), HCO manufacturer names (i.e., manufacturer descriptors for internal HCO systems such as the healthcare information system 108), —HCO manufacturer catalog number (i.e., catalog numbers used by internal HCO systems such as the healthcare information system 108), HCO vendor names (i.e., vendor names used by internal HCO systems such as the healthcare information system 108), HCO vendor catalog number (i.e., vendor catalog numbers used by internal HCO systems such as the healthcare information system 108), the last price paid for a product by the HCO, the last price paid for a product by the HCO, the amount of spending on the product by the HCO over the last 12 months, the number of purchase orders ordering the product by the HCO over the last 12 months, and the like. Product data may also include corresponding data associated with the procurement information system 110, including internal references for the procurement system that correspond to the HCO-specific references enumerated above. In some embodiments, this information is derived by the procurement information system 110 by accessing a plurality of healthcare information systems such as the healthcare information system 108.

Upon receiving a change request at the healthcare information analysis system 102, embodiments may identify one or more products associated with the change request and identify product keys associated with those products. Product keys may be transmitted to the procurement information system to obtain product data related to those products. Although change requests may include items formatted for the particular HCO, product keys may be presented in an HCO-agnostic format. In some embodiments, the healthcare information analysis system 102 may perform this translation to from a HCO-specific format to an HCO-agnostic format. Embodiments may leverage a product identification process that maps products identified in the HCO-specific format to the HCO-agnostic format by using information provided by the HCO and one or more product aliases derived from matching HCO-specific data received from other HCOs to a HCO-agnostic format. For example, embodiments may track mapping relationships which are manually or programmatically created between other HCO-specific formats and HCO-agnostic formats for other suppliers. The result of this analysis may be a confidence index for a mapping between the HCO-specific data and one or more product identifiers stored in the HCO-agnostic format. If the confidence index is greater than a threshold value, the HCO-specific data may be assigned to the product identifier stored in the HCO-agnostic format.

An example of a data flow for processing change requests via a healthcare information analysis system 102 is described below with respect to FIG. 3. FIGS. 4-12 illustrate interfaces that may be employed by a healthcare information analysis system 102 to manage a change request to a healthcare information system.

Example Apparatuses for Implementing Embodiments of the Present Invention

The healthcare information analysis system 102 may be embodied by one or more computing systems, such as apparatus 200 shown in FIG. 2. As illustrated in FIG. 2, the apparatus 200 may include a processor 202, a memory 204, input/output circuitry 206, communications circuitry 208, product management circuitry 210, request management circuitry 212, purchasing management circuitry 214, and hospital information system interface circuitry 216. The apparatus 200 may be configured to execute the operations described above with respect to FIG. 1 and below with respect to FIGS. 3-14. Although these components 202-216 are described with respect to functional limitations, it should be understood that the particular implementations necessarily include the use of particular hardware. It should also be understood that certain of these components 202-216 may include similar or common hardware. For example, two sets of circuitry may both leverage use of the same processor, network interface, storage medium, or the like to perform their associated functions, such that duplicate hardware is not required for each set of circuitry. The use of the term "circuitry" as used herein with respect to components of the apparatus should therefore be understood to include particular hardware configured to perform the functions associated with the particular circuitry as described herein.

The term "circuitry" should be understood broadly to include hardware and, in some embodiments, software for configuring the hardware. For example, in some embodiments, "circuitry" may include processing circuitry, storage media, network interfaces, input/output devices, and the like. In some embodiments, other elements of the apparatus 200 may provide or supplement the functionality of particular circuitry. For example, the processor 202 may provide processing functionality, the memory 204 may provide storage functionality, the communications circuitry 208 may provide network interface functionality, and the like.

In some embodiments, the processor 202 (and/or co-processor or any other processing circuitry assisting or otherwise associated with the processor) may be in communication with the memory 204 via a bus for passing information among components of the apparatus. The memory 204 may be non-transitory and may include, for example, one or more volatile and/or non-volatile memories. In other words, for example, the memory may be an electronic storage device (e.g., a computer readable storage medium). The memory 204 may be configured to store information, data, content, applications, instructions, or the like, for enabling the apparatus to carry out various functions in accordance with example embodiments of the present invention.

The processor 202 may be embodied in a number of different ways and may, for example, include one or more processing devices configured to perform independently. Additionally or alternatively, the processor may include one or more processors configured in tandem via a bus to enable independent execution of instructions, pipelining, and/or multithreading. The use of the term "processing circuitry" may be understood to include a single core processor, a multi-core processor, multiple processors internal to the apparatus, and/or remote or "cloud" processors.

In an example embodiment, the processor 202 may be configured to execute instructions stored in the memory 204 or otherwise accessible to the processor. Alternatively or additionally, the processor may be configured to execute hard-coded functionality. As such, whether configured by hardware or software methods, or by a combination thereof, the processor may represent an entity (e.g., physically embodied in circuitry) capable of performing operations according to an embodiment of the present invention while configured accordingly. Alternatively, as another example, when the processor is embodied as an executor of software instructions, the instructions may specifically configure the processor to perform the algorithms and/or operations described herein when the instructions are executed.

In some embodiments, the apparatus 200 may include input/output circuitry 206 that may, in turn, be in communication with processor 202 to provide output to the user and, in some embodiments, to receive an indication of a user input. The input/output circuitry 206 may comprise a user interface and may include a display and may comprise a web user interface, a mobile application, a client device, a kiosk, or the like. In some embodiments, the input/output circuitry 206 may also include a keyboard, a mouse, a joystick, a touch screen, touch areas, soft keys, a microphone, a speaker, or other input/output mechanisms. The processor and/or user interface circuitry comprising the processor may be configured to control one or more functions of one or more user interface elements through computer program instructions (e.g., software and/or firmware) stored on a memory accessible to the processor (e.g., memory 204, and/or the like).

The communications circuitry 208 may be any means such as a device or circuitry embodied in either hardware or a combination of hardware and software that is configured to receive and/or transmit data from/to a network and/or any other device, circuitry, or module in communication with the apparatus 200. In this regard, the communications circuitry 208 may include, for example, a network interface for enabling communications with a wired or wireless communication network. For example, the communications circuitry 208 may include one or more network interface cards, antennae, buses, switches, routers, modems, and supporting hardware and/or software, or any other device suitable for enabling communications via a network. Additionally or alternatively, the communication interface may include the circuitry for interacting with the antenna(s) to cause transmission of signals via the antenna(s) or to handle receipt of signals received via the antenna(s).

The product management circuitry 210 includes hardware configured to retrieve, store, and provide access to information regarding products available to a particular HCO. The product management circuitry 210 may include hardware configured to add, remove, and modify products contained within a healthcare information system, such as an item master. The product management circuitry 210 may also provide access to data related to product cross-references, including product cross-references indicated within a healthcare information system and product cross-references indicated by a procurement information system. The product management circuitry 210 may include hardware capable of receiving instruction from the request management circuitry 212 to effect change requests related to product listings within a particular healthcare information system (e.g., changes to products listed in an item master, changes to product cross-references, or the like). In some embodiments, the product management circuitry 210 may also include hardware configured to notify a procurement information system of product data stored on a hospital information system, such as to enable "crowd-sourcing" of product data from a plurality of healthcare information systems. The product management circuitry 210 may include processing circuitry, such as the processor 202, to perform these functions. The product management circuitry 210 may also include a memory, such as the memory 204 to store product data, and a communications interface, such as the communications circuitry 208 to communicate with the healthcare information system and procurement information system. The product management circuitry 210 is therefore implemented using hardware components of the apparatus configured by either hardware or software for implementing these planned functions.

The request management circuitry 212 includes hardware configured to receive a change request to perform an update to a healthcare information system. Upon receiving a change request, the request management circuitry may initiate processing that causes the healthcare information analysis system to perform certain steps of a workflow for evaluating and initiating a change associated with the change request. For example, the request management circuitry 212 may identify one or more products associated with the change request, obtain information related to the identified products via the product management circuitry 210, and generate an action plan based on the request and the obtained information. The action plan may include electronic instructions to carry out a series of tasks before committing the change to the hospital information system. Example operations for processing a change request are described further below with respect to FIGS. 3-14.

The request management circuitry 212 may include a network interface, such as the communications circuitry 208 for receiving the request from a remote system. The request management circuitry 212 may include processing circuitry, such as the processor 202 for processing a received request, for generating an action plan for implementing the request, and for taking various actions associated with the request. The request management circuitry 212 may store request data, action plans, request status data, and the like in a memory, such as the memory 204. The request management circuitry 212 is therefore implemented using hardware components of the apparatus configured by either hardware or software for implementing these planned functions.

The purchasing management circuitry 214 includes hardware configured to monitor transactions performed by healthcare information systems, including purchase of products from suppliers. In some embodiments, the purchasing management circuitry 214 may monitor transactional traffic data between a healthcare information system and a procurement information system as the HCO orders products from the procurement information system. Alternatively, in some embodiments the purchasing management circuitry 214 may receive transactional traffic data information directly from the healthcare information system and/or procurement information system. In yet further embodiments, transactional traffic data may be received in a processed or analyzed format, while in other embodiments the transactional traffic data may be received as raw purchase order data, invoice data, or the like. The transactional traffic data may be received via a network interface, such as the communications circuitry 208. Processing and managing of transactional traffic data may be performed via processing circuitry, such as the processor 202. Transactional traffic data may be stored in a memory, such as the memory 204. The purchasing management circuitry 214 is therefore implemented using hardware components of the apparatus configured by either hardware or software for implementing those planned functions.

The hospital information system interface circuitry 216 includes hardware configured to communicate with hospital information systems, such as item masters, charge masters, formularies, and the like. The hospital information system interface circuitry 216 may implement changes to said hospital information systems based on change requests processed by the healthcare information analysis system. The hospital information system interface circuitry 216 may communicate with the hospital information system via a network interface, such as the communications circuitry 208. The hospital information system interface circuitry 216 includes processing circuitry, such as the processor 202, to implement changes to the hospital information systems, such as changes related to a request processed by the request management circuitry 212. The hospital information system interface circuitry 216 is therefore implemented using hardware components of the apparatus configured by either hardware or software for implementing those planned functions.

As will be appreciated, any such computer program instructions and/or other type of code may be loaded onto a computer, processor or other programmable apparatus's circuitry to produce a machine, such that the computer, processor other programmable circuitry that execute the code on the machine create the means for implementing various functions, including those described herein.

It is also noted that all or some of the information presented by example displays described herein can be based on data that is received, generated and/or maintained by one or more components of the apparatus 200. In some embodiments, one or more external systems (such as a remote cloud computing and/or data storage system) may also be leveraged to provide at least some of the functionality discussed herein.

As described above and as will be appreciated based on this disclosure, embodiments of the present invention may be configured as methods, mobile devices, backend network devices, and the like. Accordingly, embodiments may comprise various means including entirely of hardware or any combination of software and hardware. Furthermore, embodiments may take the form of a computer program product on at least one non-transitory computer-readable storage medium having computer-readable program instructions (e.g., computer software) embodied in the storage medium. Any suitable computer-readable storage medium may be utilized including non-transitory hard disks, CD-ROMs, flash memory, optical storage devices, or magnetic storage devices.

Example Electronic Marketing Information Service Data Flow

FIG. 3 depicts an example data flow 300 illustrating interactions between healthcare information systems, a healthcare information analysis system 302, and a procurement information system. The healthcare information analysis system 302 may be implemented in the same or a similar fashion as the healthcare information analysis system 102 as described above with respect to FIG. 1 and/or the apparatus 200 described above with respect to FIG. 2.

The data flow 300 illustrates electronic data may be received and processed by different components of a healthcare information analysis system 302 to process a change request. The healthcare information analysis system 302 may receive a set of request parameters 304 which are processed by request management circuitry 306. The request parameters 304 may include a variety of parameters related to a change to be implemented to a hospital information system. For example, the request parameters 304 may include identification of particular products to be added to a hospital information system, a reason for the request (e.g., the request will result in a clinical improvement, improved revenue, standardization of products, an operational improvement, or the like), a timeline for the request, one or more product cross-references, one or more document attachments, information about the requester, or the like. In some embodiments, the request parameters may be dynamically defined by an administrator or other user creating the request.

The request management circuitry 306 may process the request and instruct other elements of the healthcare information analysis system 302 to obtain data necessary to review, verify, and validate the request before initiating the change to the hospital information system. To perform these actions, the request management circuitry 306 may communicate with transactional management circuitry 310 and product management circuitry 316 to obtain electronic data related to the change request.

The transactional management circuitry 310 may receive and monitor transactional traffic data 308 as part of processing the change request. The transactional traffic data 308 may indicate which products are purchased by a particular HCO, whether the HCO purchases any products associated with the request or cross-references for products associated with the request, the price paid for products associated by the request, the volume of products purchased, invoice data for received products, and other data related to transactions performed by the HCO. In some embodiments, invoice data is correlated to purchase order data to determine whether and when purchase orders are fulfilled.

The product management circuitry 316 may obtain electronic data for products associated with the request. The product management circuitry 316 may obtain internal product data 312 and external product data 314. The internal product data 312 may include data for products received from hospital information systems, such as item masters, lists of cross-references, and the like. The external product data 314 may include product data received from external systems such as a procurement information system. The procurement information system may provide lists of products that are available from suppliers in communication with the procurement information system, lists of cross-references used by other HCOs in communication with the procurement information system, or the like.

The request management circuitry 306 may store request data 320 on the healthcare information analysis system 302. The stored request data 320 may include action plans, feedback, implementation data, product data, and other information related to one or more received, pending, or completed requests. For example, processing of a particular request may require verification or feedback from a particular set of users or administrators, and as approval is received from each user, the healthcare information analysis system 302 may store that approval. Similarly, a given request may include attached documents, virtual meeting notifications, electronic communications, and the like.

The request management circuitry 306 may control implementation of a particular request. Particular types of requests may include particular action items, tasks, meetings, approvals, and the like which, upon receiving a request related to a particular product or healthcare information system, are used to generate an implementation plan for the request. The request management circuitry 306 may then oversee the particular tasks related to implementation of the task and, upon completion of those tasks, notify hospital information system interface circuitry 318. The hospital information system interface circuitry 318 may generate request implementation data 322. The request implementation data 322 may include instructions to one or more hospital information systems to implement changes associated with the request, such as adding or removing items to an item master, adding or removing item cross-references, and/or the like. In some embodiments, the request implementation data 322 may include instructions, action plans, executable code, or the like for implementing the change to the healthcare information system.

Exemplary Interfaces

FIGS. 4-12 illustrate exemplary interfaces for implementing a workflow for effecting a change to a healthcare information system in accordance with exemplary embodiments of the present invention. The interfaces depicted in FIGS. 4-12 may be provided by a healthcare information analysis system in a variety of manners. For example, the healthcare information analysis system may provide a web-based interface allowing users to interact with the healthcare information analysis system via a web browser.

Figure 4:
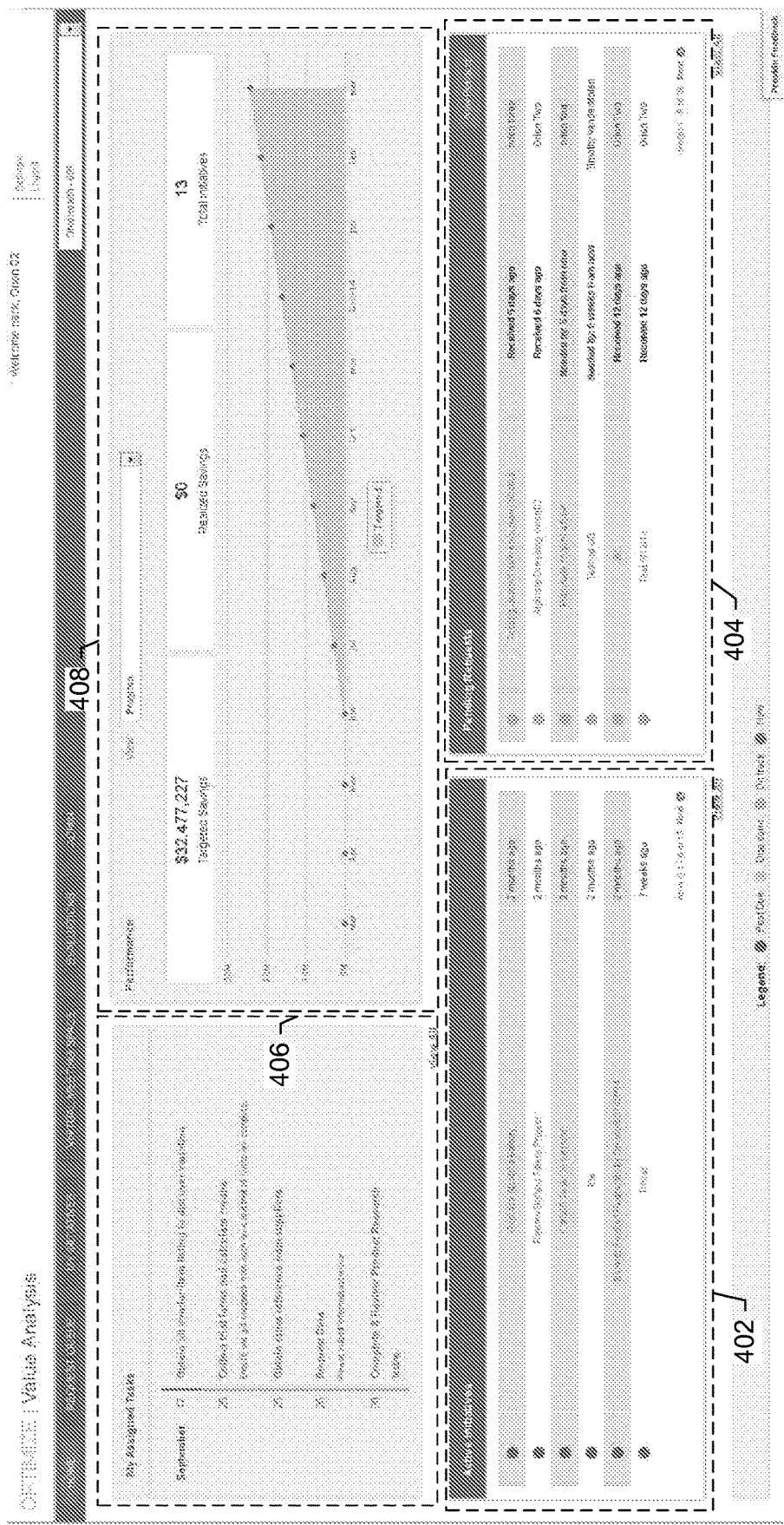

FIG. 4 illustrates an example dashboard interface 400 for interacting with a healthcare information analysis system in accordance with some exemplary embodiments. The dashboard interface 400 provides a list of ongoing initiatives under evaluation 402, a list of pending change requests 404, a list of tasks 406, and an overall savings number 408. Once a request has been evaluated and assigned to one or more users for implementation, the request may be reclassified as an initiative. The list of tasks 406 may include a list of action items and other pending actions and tasks associated with previously processed change requests. The overall savings number 408 may provide a graphical representation of the total savings achieved as a result of previously processed change requests.

Figure 5:
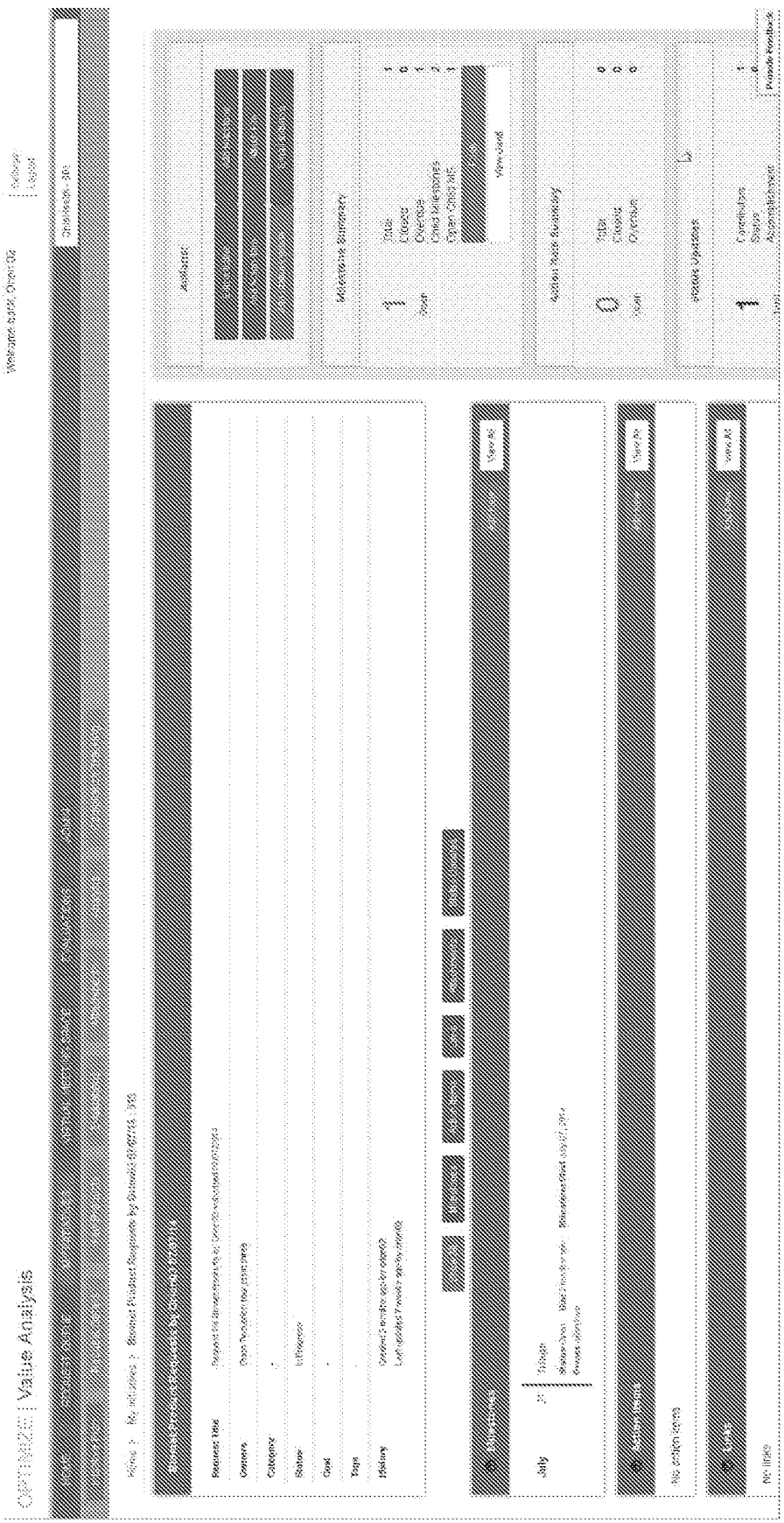

FIG. 5 illustrates an exemplary interface 500 for viewing an initiative status in accordance with some embodiments of the present invention. The interface 500 includes a set of menus and interface controls for viewing the action items, products, milestones, attachments, and other data related to a particular change request. In the present context, the term "initiative" may be understood to refer to a change request that has been approved for evaluation prior to being accepted.

Figure 6:
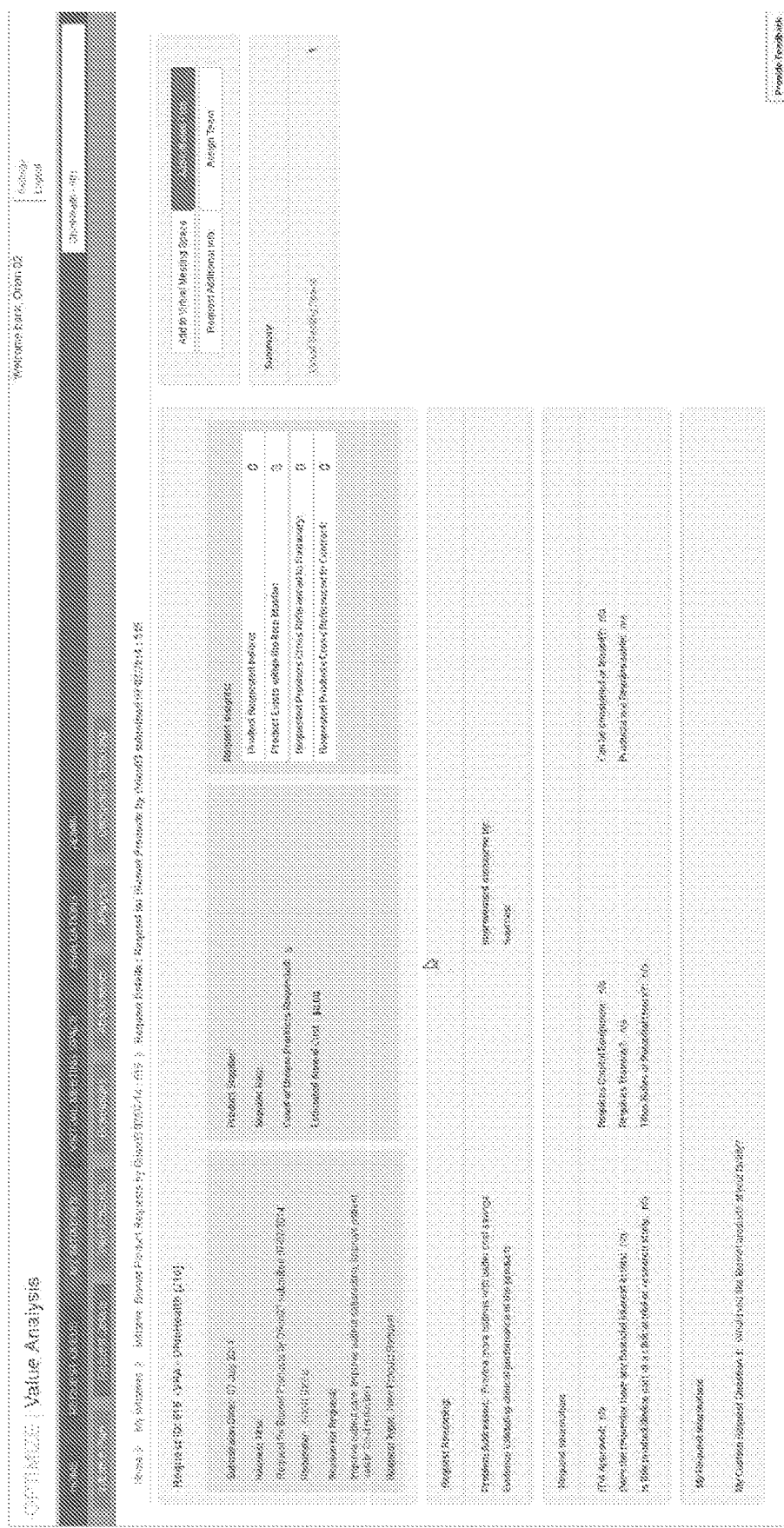

FIG. 6 illustrates an exemplary interface 600 for viewing the details of a particular request. As noted above, requests may be reclassified as initiatives upon approval. Accordingly, the information displayed in the request interface may be the same or similar to the information displayed in the initiative status interface 500.

Figure 7:
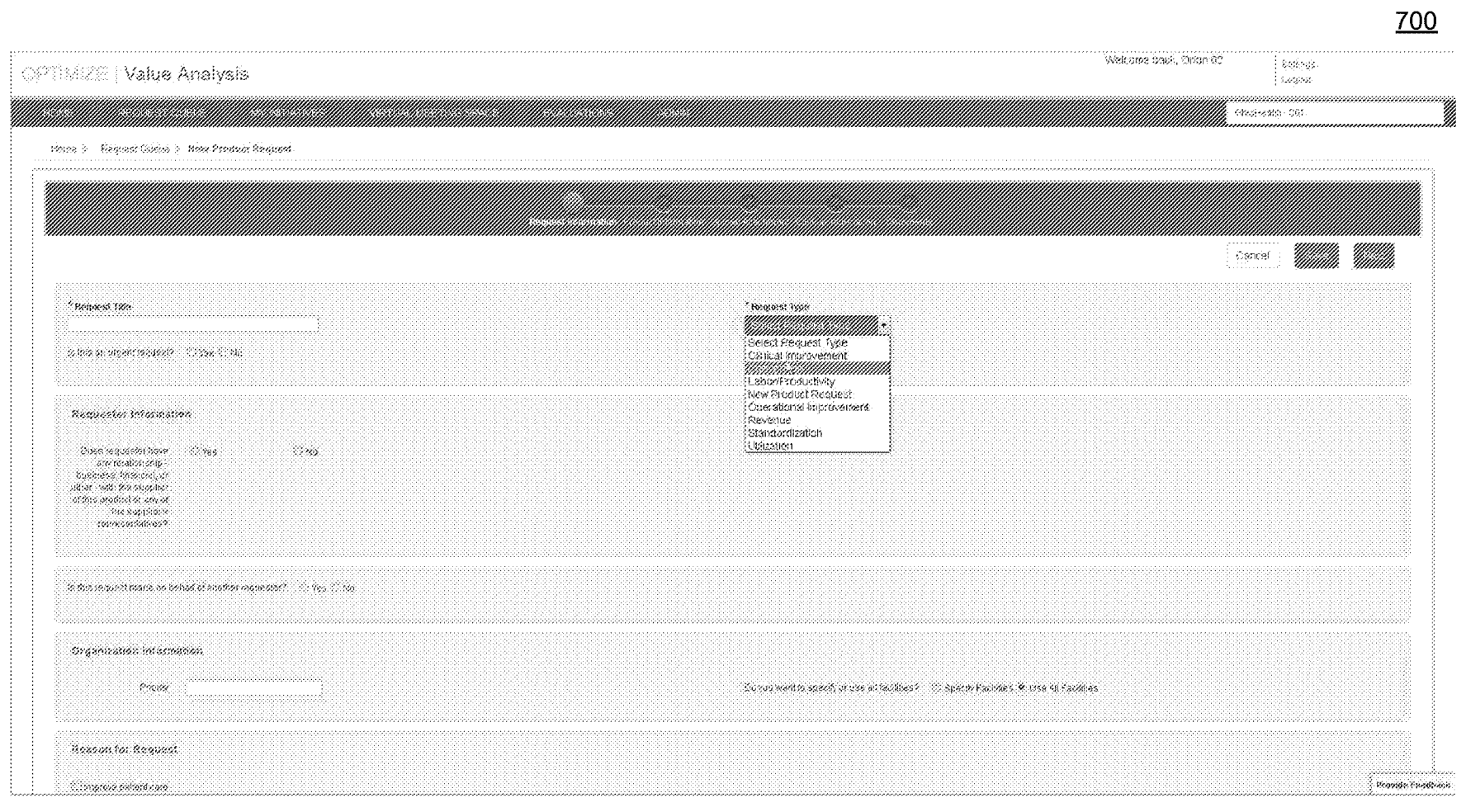

FIG. 7 illustrates an exemplary interface 700 for initiating a request in accordance with some embodiments of the present invention. The interface 700 includes interface controls for entering a request title, selecting a request type, providing information about the request, providing information about the HCO, and the like. The interface 700 may allow users to indicate the purpose of the request (e.g., clinical improvement, product conversion, productivity improvement, new product request, operational improvement, improved revenue, improved product standardization, improved utilization, or the like).

Figure 8:
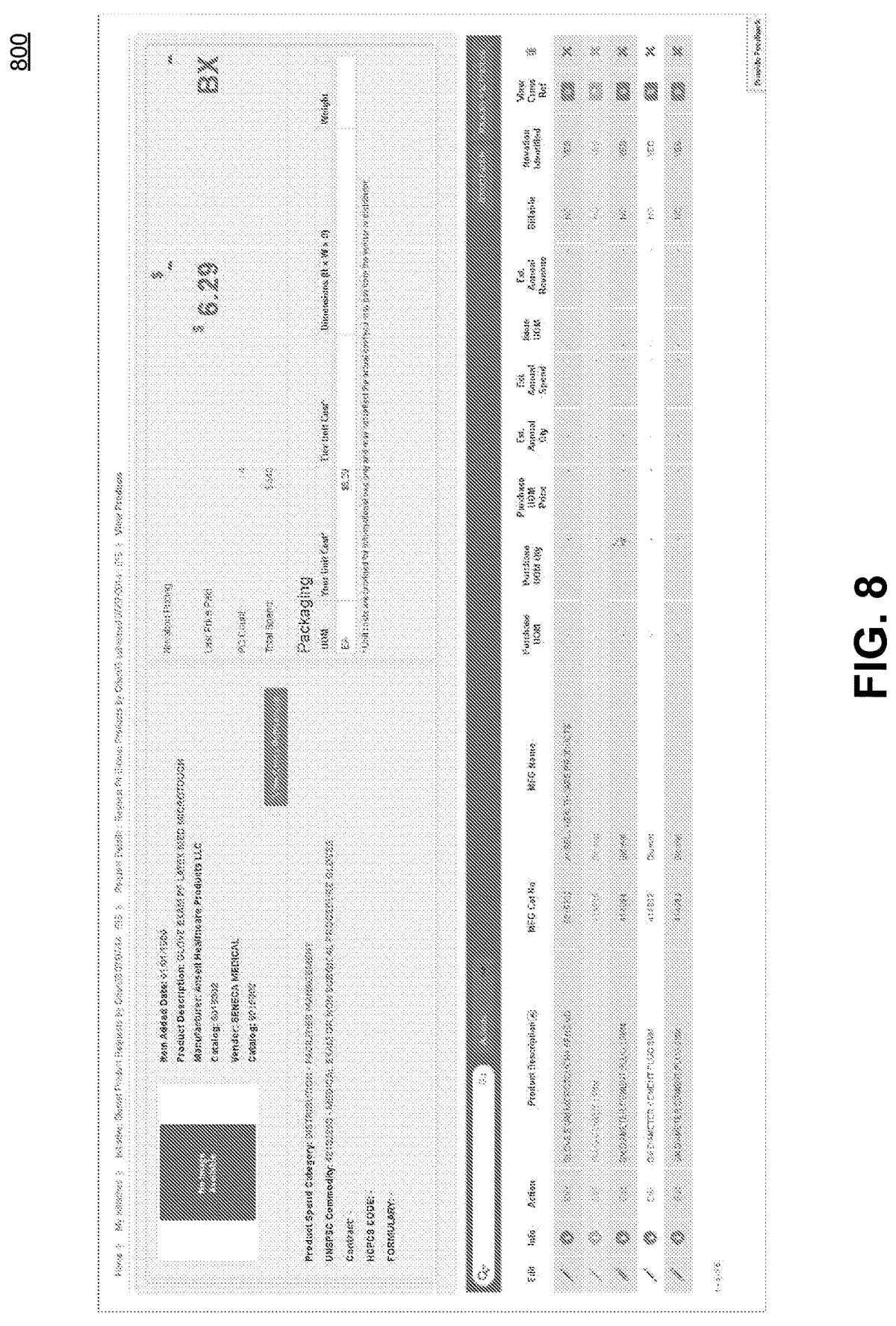

FIG. 8 illustrates an exemplary interface 800 for selecting products to be associated with a request. The products selected may be provided by an external source, such as a procurement information system as described above with respect to FIGS. 1 and 3. The interface 800 may include controls for selecting products by category, UNSPSC numbers, manufacturer identifiers, and the like. The interface 800 may also provide pricing information for selected products, cross-reference information for selected products, recent transaction information for the selected products, and the like.

Figure 9:
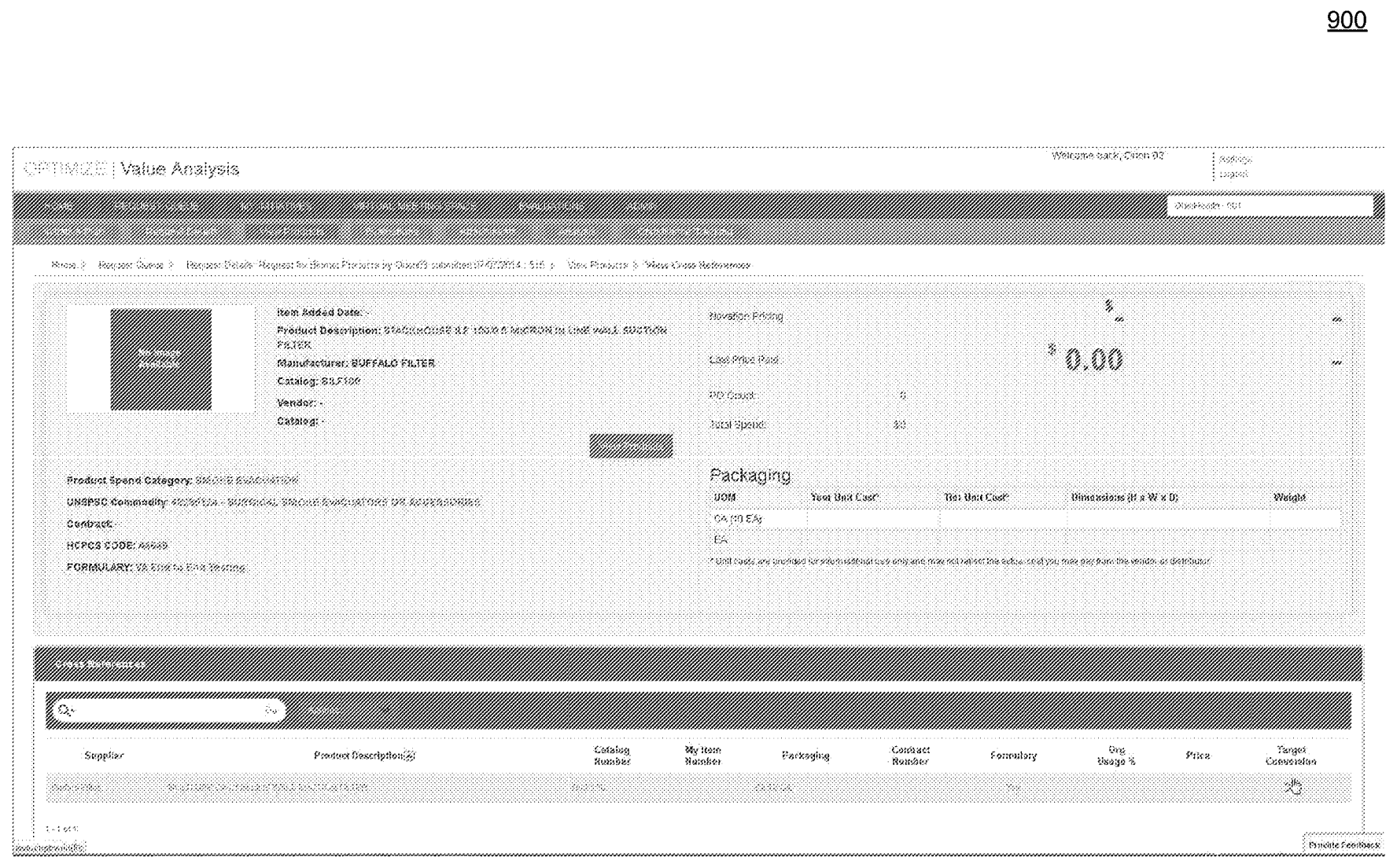

FIG. 9 illustrates an exemplary interface 900 for viewing cross-references for a particular product associated with a request in accordance with exemplary embodiments of the present invention. The interface 900 provides users with the ability to view and search for cross-references for a particular product involved in a request.

Figure 10:
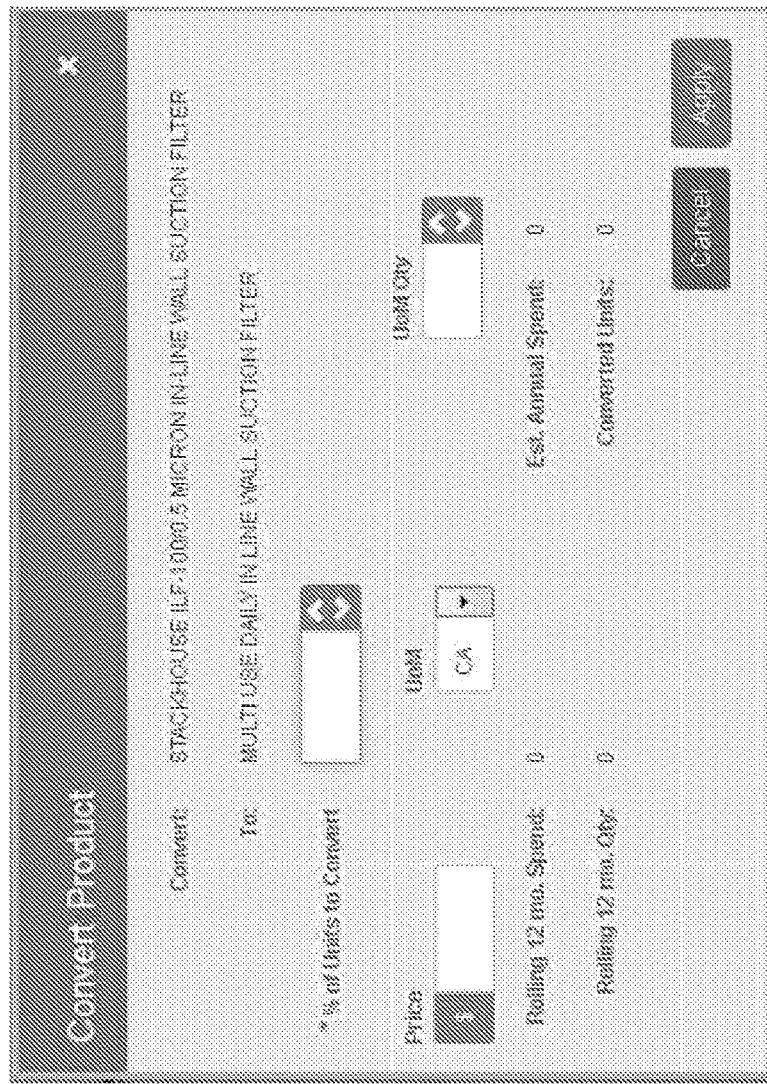

FIG. 10 illustrates an exemplary interface 1000 for entering data related to a product conversion request in accordance with embodiments of the present invention. The interface 1000 allows users to evaluate the impact of changing from a particular product to a different product, such as a valid product cross-reference. Once data regarding the conversion has been entered into the interface 1000, data related to the request may be updated to reflect the change.

Figure 11:
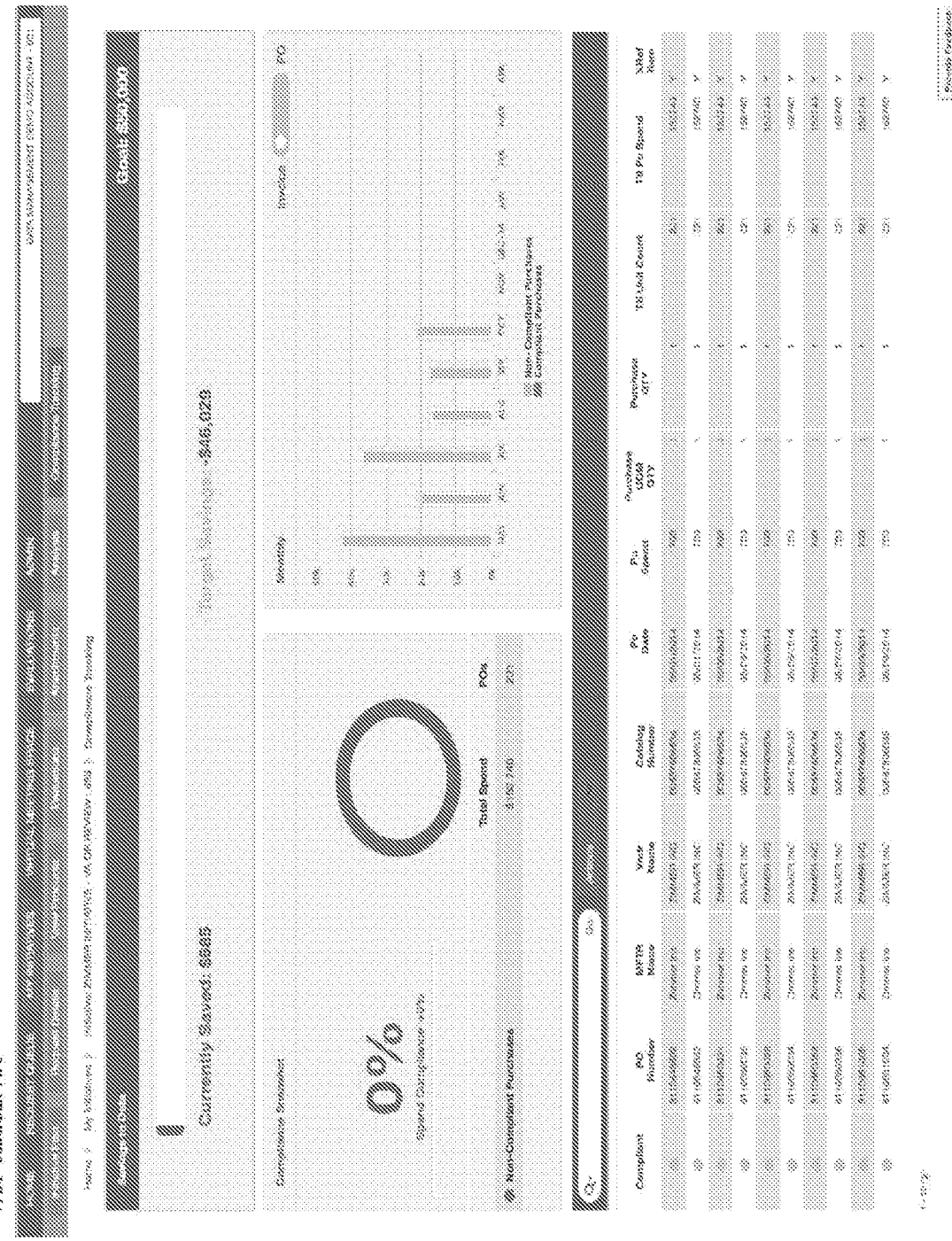

FIG. 11 illustrates an exemplary interface 1100 for monitoring compliance with a change initiative in accordance with embodiments of the present invention. The interface 1100 provides analytics derived from monitored spending to show if and whether transactions performed by a HCO are compliant with changes processed through the healthcare information analysis system.

Figure 12:

FIG. 12 illustrates an exemplary interface 1200 for calculating and notifying users of a total benefit derived from a particular change request or initiative. In some embodiments, the financial benefits may be provided through manual data entry by a user, while in other embodiments such financial benefits may be automatically calculated based on cost savings or cost increases associated with actions performed which impact product selection and purchasing decisions.

Exemplary Processes for Implementing a Healthcare Information Analysis System

FIGS. 13-14 illustrate flow diagrams depicting processes for implementing the healthcare information analysis system described above with respect to FIGS. 1-12 to implement changes to healthcare information systems in accordance with exemplary embodiments of the present invention.

FIG. 13 illustrates a flow diagram depicting an example of a process 1300 for processing a request and reporting the results of the request in accordance with embodiments of the present invention. The process 1300 illustrates how requests may be submitted to a healthcare information analysis system and processed by the healthcare information analysis system to effect change in one or more healthcare information systems. The process 1300 may be performed by a healthcare information analysis system, such as apparatus 200 described above with respect to FIG. 2.

At action 1302, request parameters are received that indicate at least one product change. As described above, the request parameters may identify one or more products for evaluation for causing a change in a hospital information system. At action 1304, product data associated with the request parameters may be identified. Identification of product data may be performed by determining a product key for products contained within the change request. The product key may be used to perform a lookup operation using a procurement information system. The procurement information system may provide information related to the product such as manufacturer information, cost information, completed assessments and questionnaires related to the product, and the like.

At action 1306, an action plan for implementing the request may be generated based at least in part on the product data. The process 1300 may allow for manual definition of tasks and actions related to implementation of the request. For example, a request to add a product to a formulary may include notifying particular stakeholders of the intent to add the new product via an electronic notification, such as an email, designating particular stakeholders to approve or deny the addition of the product, initiation of one or more studies to evaluate the efficacy of the product, updating one or more materials management systems to reflect the new addition to the formulary, or the like.

At action 1308, one or more healthcare information systems are programmatically updated based on the action plan. In some embodiments, the healthcare information systems are updated automatically in response to completion of the action plan identified at action 1306. At action 1310, implementation of the request is monitored by monitoring transaction data created by the healthcare information system. The transaction data may include product purchase orders, product invoices, and the like to determine which products have been purchased by the HCO to verify that the HCO is in compliance with the change request. At action 1312, the results of the monitoring operation at action 1310 are reported to verify compliance with the change request.

FIG. 14 illustrates a flow diagram depicting an example process 1400 for implementing a request action plan in accordance with exemplary embodiments of the present invention. The process 1400 illustrates how embodiments of the present invention can provide for management of a collaborative workflow that receives input from multiple stakeholders prior to initiating a change to evaluate the impact of the change. The process 1400 may be performed by a healthcare information analysis system, such as apparatus 200 described above with respect to FIG. 2.

At action 1402, a request action plan is received. As described above with respect to FIG. 13, a request action plan may be derived based on a set of request parameters and a set of product data associated with a product indicated in the request parameters. At action 1404, one or more stakeholders associated with the action plan may be identified. Stakeholders may be identified within the request itself, manually identified by users of the healthcare information analysis system, or programmatically identified based on assigned user roles for users of the healthcare information analysis system. For example, a request of a certain type may require user input from users with particular roles (e.g., hospital administrator, clinician, procurement manager) for particular actions. Upon receiving the action plan, users of each role for which actions are defined in the action plan may be notified. In some embodiments, specific users may be associated with the action plan.

At action 1406, the identified stakeholders are electronically notified of their role in processing the request. The stakeholders may be notified by email, for example, or by a notification on a login page or dashboard associated with the healthcare information analysis system. At action 1408, electronic feedback is received from the notified stakeholders. For example, stakeholders may provide feedback via surveys, questionnaires, assessments, and the like. In some embodiments, received feedback may be provided to an external system, such as a procurement information system, to be associated with a particular product or category. Such information may be tied to products such that future requests may also provide such data for use in evaluating those future requests. In some embodiments, the healthcare information analysis system may also include other mechanisms for collaboration and providing feedback, such as the ability to conduct virtual meetings, the ability to assign particular users to particular action items, the ability to attach documents to particular requests, and the like. In some embodiments, approval may be required from particular users, from particular groups of users, or users with particular roles to indicate that a given action has been completed.

At action 1410, elements of the action plan or particular tasks may be implemented based on the results of the received feedback. For example, particular tasks may be marked as complete or incomplete based on the feedback, other tasks may be added, tasks may be removed, or the like. Generally, implementation of a change request may not be considered to be complete until all tasks associated with the action plan have been completed. Upon completion of the action plan, embodiments may propagate changes to healthcare information systems to confirm or complete the change request.

As will be appreciated, computer program code and/or other instructions may be loaded onto a computer, processor or other programmable apparatus's circuitry to produce a machine, such that execution of the code on the machine by the computer, processor, or other circuitry creates the means for implementing various functions, including those described herein.

As described above and as will be appreciated based on this disclosure, embodiments of the present invention may be configured as methods, mobile devices, backend network devices, and the like. Accordingly, embodiments may comprise various means including entirely of hardware or a combination of software and hardware. Furthermore, embodiments may take the form of a computer program product on at least one computer-readable storage medium having computer-readable program instructions (e.g., computer software) embodied in the storage medium. Any suitable computer-readable storage medium may be utilized, including non-transitory hard disks, CD-ROMs, flash memory, optical storage devices, magnetic storage devices, or the like.

Embodiments of the present invention have been described above with reference to block diagrams and flowchart illustrations of methods, apparatuses, systems and computer program products. It will be understood that each block of the circuit diagrams and process flowcharts, and combinations of blocks in the circuit diagrams and process flowcharts, respectively, can be implemented by various means including computer program instructions. These computer program instructions may be loaded onto a general purpose computer, special purpose computer, or other programmable data processing apparatus to produce a machine, such that the computer program product includes the instructions which execute on the computer or other programmable data processing apparatus create a means for implementing the functions specified in the flowchart block or blocks.

These computer program instructions may also be stored in a computer-readable storage device that can direct a computer or other programmable data processing apparatus to function in a particular manner, such that the instructions stored in the computer-readable storage device produce an article of manufacture including computer-readable instructions for implementing the function discussed herein. The computer program instructions may also be loaded onto a computer or other programmable data processing apparatus to cause a series of operational steps to be performed on the computer or other programmable apparatus, thereby producing a computer-implemented process such that the instructions executed on the computer or other programmable apparatus cause performance of the steps and thereby implement the functions discussed herein.

Accordingly, blocks of the block diagrams and flowchart illustrations support combinations of means for performing the specified functions, combinations of steps for performing the specified functions and program instruction means for performing the specified functions. It will also be understood that each block of the circuit diagrams and process flowcharts, and combinations of blocks in the circuit diagrams and process flowcharts, can be implemented by special purpose hardware-based computer systems that perform the specified functions or steps, or combinations of special purpose hardware and computer instructions.

Many modifications and other embodiments of the inventions set forth herein will come to mind to one skilled in the art to which these embodiments of the invention pertain having the benefit of the teachings presented in the foregoing descriptions and the associated drawings. Therefore, it is to be understood that the embodiments of the invention are not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A healthcare information analysis system comprising:
    a server configured to communicate with an electronic healthcare information system;
    a processor and a non-transitory computer readable medium, the non-transitory computer readable medium comprising instructions stored thereon that when executed by the processor configure the healthcare information analysis system to:
        monitor, via the server, electronic purchases of one or more current products by a healthcare organization (HCO);
        receive, via the server, HCO-specific data regarding one or more different products available for purchase by the HCO from the electronic healthcare information system;
        map, via the processor, each of the one or more different products in the HCO-specific data to a HCO-agnostic product identifier;
        modify the HCO-specific data by translating the HCO-specific data from an initial format of the HCO-specific data to a HCO-agnostic format, the initial format of the HCO-specific data being a different format than the HCO-agnostic format, wherein the HCO-agnostic product identifier is stored in the non-transitory computer readable medium in the HCO-agnostic format;
        analyze, via the processor, the HCO-specific data and one or more HCO-agnostic product identifiers stored in the non-transitory computer readable medium in the HCO-agnostic format;
        generate, via the processor, a confidence index between the HCO-specific data and one or more product identifiers stored in the non-transitory computer readable medium in the HCO-agnostic format;

assign, via the processor, the HCO-specific data to the HCO-agnostic product identifier stored in the non-transitory computer readable medium in the HCO-agnostic format when the confidence index is greater than a threshold value;

generate, via the processor, an electronic file in an Electronic Data Interchange (EDI) format, the electronic file comprising information corresponding to the assignment of the HCO_specific data to the HCO-agnostic product identifier; and communicate, via the processor, the electronic file to the electronic healthcare information system, the communication causing automatic propagation of changes to information within the electronic healthcare information system, the propagated changes comprising modifications to information based on the assignment of the HCO specific data to the HCO-agnostic product identifier.

2. The healthcare information analysis system of claim 1, wherein the instructions further configure the healthcare information analysis system to:

propagate a deactivation of the one or more products stored in the non-transitory computer readable medium in the healthcare information analysis system to the healthcare information system.

3. The healthcare information analysis system of claim 1, calculate a financial impact of the result of at least one change to the electronic purchases of the one or more current products.

4. The healthcare information analysis system of claim 3, wherein the instructions further configure the healthcare information analysis system to:

display a web-based interface configured to allow users to interact with the healthcare information analysis system via a web browser.

5. The healthcare information analysis system of claim 4, wherein the web-based interface is configured to display the financial impact.

6. The healthcare information analysis system of claim 5, wherein the instructions further configure the healthcare information analysis system to:

using the processor, implement the change to the healthcare information system.

7. The healthcare information analysis system of claim 6, wherein the at least one change comprises changes to at least one of an electronic item masters, item formularies, and charge masters.

* * * * *